US008288138B2

(12) United States Patent
Birkmire et al.

(10) Patent No.: US 8,288,138 B2
(45) Date of Patent: Oct. 16, 2012

(54) CONVERSION OF BIOMASS INTO ETHANOL

(75) Inventors: Scott Birkmire, Denver, CO (US); Chris Lindeman, Lakewood, CO (US); Brian Duff, Evergreen, CO (US); Jesse Spooner, Gilman, WI (US); Mark Yancey, Denver, CO (US)

(73) Assignee: NEAtech, LLC, Denver, CO (US)

( * ) Notice: Subject to any disclaimer, the term of this patent is extended or adjusted under 35 U.S.C. 154(b) by 508 days.

(21) Appl. No.: 12/510,744

(22) Filed: Jul. 28, 2009

(65) Prior Publication Data

US 2010/0196979 A1   Aug. 5, 2010

Related U.S. Application Data

(60) Provisional application No. 61/084,859, filed on Jul. 30, 2008.

(51) Int. Cl.
*C12P 7/06* (2006.01)
*C12M 1/00* (2006.01)
*C07C 29/80* (2006.01)

(52) U.S. Cl. .................. 435/161; 435/290.1; 203/19

(58) Field of Classification Search .................. 435/161, 435/290.1; 203/19
See application file for complete search history.

(56) References Cited

U.S. PATENT DOCUMENTS

| 4,309,254 | A  | * | 1/1982 | Dahlstrom et al. ............. 203/47 |
| 5,411,594 | A  |   | 5/1995 | Brelsford |
| 6,444,437 | B1 |   | 9/2002 | Sporleder et al. |
| 2009/0093027 | A1 | | 4/2009 | Balan et al. |

FOREIGN PATENT DOCUMENTS

EP          169068 A2 *  1/1986

OTHER PUBLICATIONS

Willington et al., "Options for handling stillage waste from sugar-based fuel ethanol production," Resources and Conservation 8:111-129, 1982.*

* cited by examiner

*Primary Examiner* — Rosanne Kosson

(57) ABSTRACT

A process and system for the conversion of biomass, such as spent brewers grain, into ethanol and other commercial products, such as pelletized fuel, biogas, fertilizer, and livestock feed, is disclosed. The method may include biomass pretreatment, hydrolysis, fermentation, distillation, and dehydration phases.

9 Claims, 3 Drawing Sheets

CONVERSION OF BIOMASS INTO ETHANOL

RELATED APPLICATIONS

This application claims the benefit under 35 U.S.C. §119 (e) of U.S. Provisional Patent Application Ser. No. 61/084,859, filed Jul. 30, 2008, and titled "Conversion of Brewery Biomass Waste into Fuel Ethanol and Livestock Feed," which is incorporated herein by reference in its entirety.

TECHNICAL FIELD

The present disclosure relates generally to energy production from biomass sources. More specifically, the present disclosure relates to the use of spent brewers grain biomass for the production of ethanol.

SUMMARY OF THE INVENTION

The invention is directed to processes for converting a grain fermentation residual product into ethanol.

In one embodiment, the process includes pretreating a grain fermentation residual product with acid and heat to degrade hemicellulosic material within the grain fermentation residual product. In this case, pretreating the grain fermentation residual product includes an in-line processing system that involves treating the grain fermentation residual product with acid to form an acidified grain material; steam-heating the acidified grain material in a pressurized pipe, to a temperature of between about 325° F. to about 375° F. and a pressure of between about 80 to about 170 psig; flowing the heated and acidified grain material through a throttle valve into a reaction vessel slightly above atmospheric pressure; neutralizing the grain material in the reaction vessel; adding a liquid brewery feedstock or water to provide a mixed material stream; and cooling the mixed material stream to a temperature of between about 130° F. to about 150° F. with an in-line pipe heat exchanger. The process further includes hydrolyzing the pretreated grain fermentation residual product with an enzyme to convert starch and cellulosic material to simple sugars; fermenting the simple sugars into ethanol with an ethanol-producing microbe; distilling the ethanol; dehydrating the ethanol to remove water; and recovering whole stillage as an animal or fish feed product.

In another embodiment, the process includes pretreating a grain fermentation residual product with acid and heat to degrade hemicellulosic material within the grain fermentation residual product. The process also includes hydrolyzing the pretreated grain fermentation residual product with an enzyme to convert starch and cellulosic material to simple sugars. The process further includes fermenting the simple sugars into ethanol with an ethanol-producing microbe. The process also includes distilling the ethanol with a single distillation column to provide an ethanol/water mixture of between about 35% to about 60% w/w ethanol, and dehydrating the ethanol to remove water by flowing the ethanol/water mixture from the single distillation column through a series of three pervaporative membranes to remove water from the ethanol. Finally, the method includes recovering whole stillage as an animal or fish feed product.

In yet another embodiment, the process includes pretreating a grain fermentation residual product with acid and heat to degrade hemicellulosic material within the grain fermentation residual product. The process also includes hydrolyzing the pretreated grain fermentation residual product with an enzyme to convert starch and cellulosic material to simple sugars. The process further includes fermenting the simple sugars into ethanol with an ethanol-producing microbe. The method also includes distilling the ethanol with a single distillation column to provide an ethanol/water mixture of between about 35% to about 60% w/w ethanol, and dehydrating the ethanol to remove water by treating the ethanol/water mixture with molecular sieves to remove water from the ethanol. Finally, the method includes recovering whole stillage as an animal or fish feed product.

The processes may also include denaturing the dehydrated ethanol for the production of fuel ethanol.

The grain fermentation residual product may include spent brewers grain and/or residual distiller grain products.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
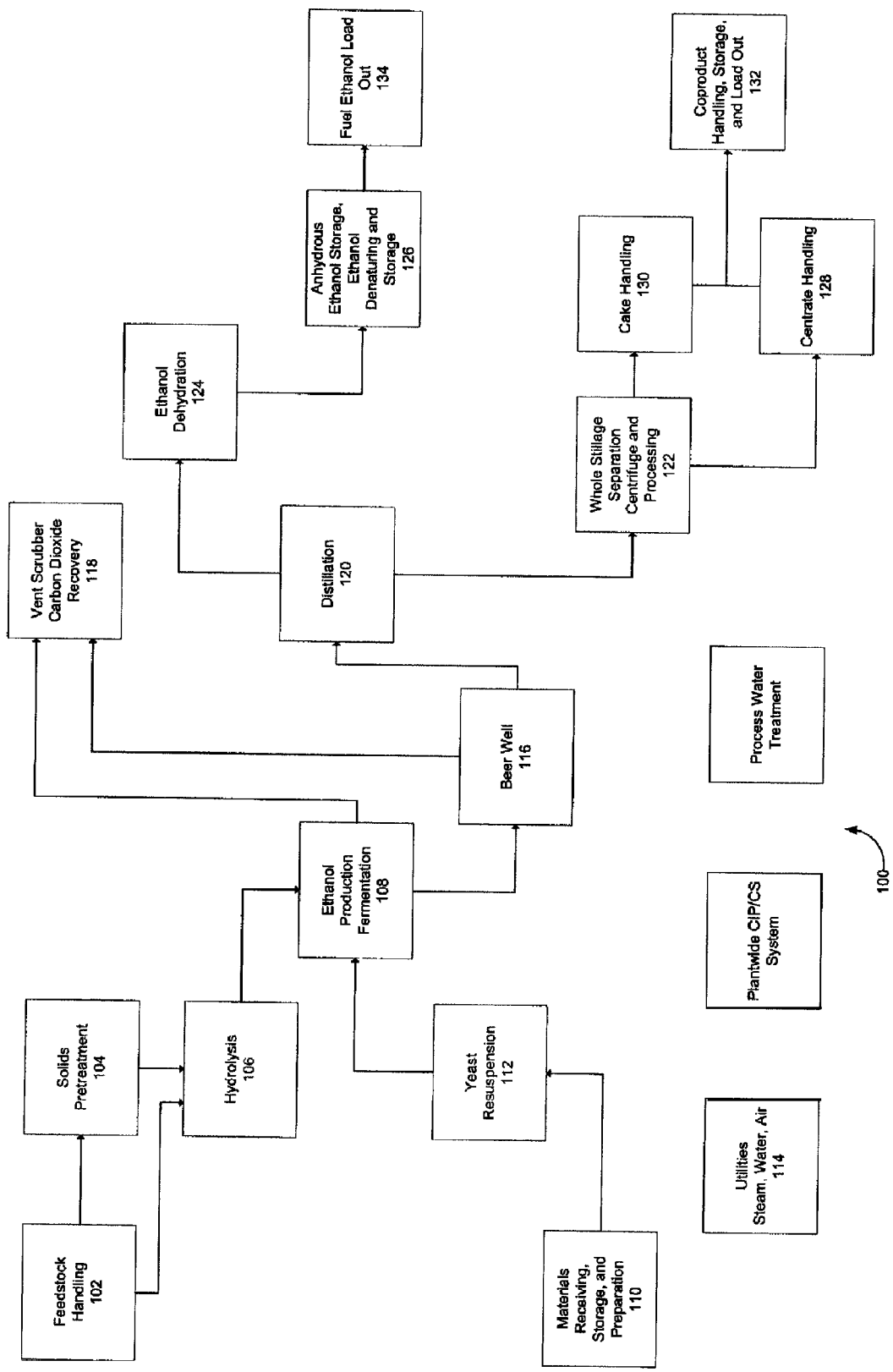
FIG. 1 is a block diagram of one embodiment of a process for converting spent brewers grain into ethanol.

Increasing energy demands often lead to the development of alternative energy resources. Biomass resources have been developed for this purpose, such as the production of ethanol from corn. However, the growing concern over the use of corn for fuel rather than food has prompted the use of other biomass materials for energy production. An alternative form of biomass for use in ethanol production is from lignocellulosic feedstocks. Lignocellulose has three main components, those being cellulose, hemicellulose, and lignin. Depending on the source of the lignocellulose, the proportions of the three components may vary. Cellulose and hemicellulose are carbohydrate oligomers, and are covalently bound to the lignin component. The lignin component is made up of substituted phenols, and acts as a glue to keep the components together. The use of lignocellulosic feedstocks has been limited due to the cost involved in pretreating lignocelluloses to separate the cellulose and hemicellulose components from the lignin, which may make it more amenable to ethanol processing. Furthermore, the cost of accumulating large quantities of material has slowed the use of lignocellulosic material.

The production of spent brewers grain ("SBG") and additional residual brewing products at a brewery, provides a centrally located source of lignocellulosic material. The brewing process also provides a type of pretreatment of the material, making the feedstock more amendable to energy conversion. Furthermore, a brewery facility can supply shared utilities, such as steam, electric, air, cooling water, and waste water treatment, to a biomass conversion plant, if the plant is connected to the brewery. The biomass conversion plant can also supply, for example, heat, water, power, or waste water treatment, to the brewery. The brewery provides several lignocellulosic feedstocks that may be used for conversion to ethanol using an enzymatic hydrolysis conversion. The feedstocks can be processed to generate various products, including ethanol, an enhanced high-protein animal feed, carbon dioxide, methane, fertilizer, and a fibrous material capable of being pelletized for fuel use.

It will be readily understood that the components of the embodiments as generally described and illustrated in the Figures herein could be arranged and designed in a wide variety of different configurations. The following more detailed description of various embodiments, as represented in the Figures, is not intended to limit the scope of the present disclosure, but is merely representative of one embodiment.

The order of the steps or actions of the methods described in connection with the embodiments disclosed herein may be changed by those skilled in the art without departing from the scope of the present disclosure. In other words, unless a specific order of steps or actions is required for proper operation of the embodiment, the order and/or use of specific steps and/or actions may be modified. Thus, any order in the Figures or detailed description is for illustrative purposes only and is not meant to imply a required order.

For this application, the phrases "connected to" and "coupled to" refer to any form of interaction between two or more entities, including mechanical, electrical, magnetic, electromagnetic, fluid, and thermal interaction. Two components may be coupled to each other even though they are not in direct contact with each other.

FIG. 1 represents one embodiment of a process 100 for converting SBG to ethanol. The exemplary process 100 includes several phases, including: feedstock handling 102, solids pretreatment 104, hydrolysis 106, fermentation 108, carbon dioxide recovery 118, distillation 120, dehydration 124, whole stillage processing 122, and product storage and/or loadout 132. The feedstock handling phase 102 may include equipment to receive, store, and mix both solid and liquid feedstocks from a brewery. The primary feedstock is spent brewers grain, which may be approximately 85% of the material. The remaining feedstock materials may include Dust and Sprouts ("DS"), Brewer's Condensed Solubles ("BCS"), and Trub. SBG and DS are solid feedstocks and Trub and BCS are liquid feedstocks, which are delivered and handled accordingly.

In certain embodiments, the solid feedstock may be milled and then blended with the liquid feedstock. If necessary, this mixture can be slurried with water.

In one embodiment, given the nature of the solid and liquid feedstocks, they are handled separately in the feedstock handling phase 102, and combined for hydrolysis 106 (to be discussed infra). Upon receipt, the liquid feedstock may pass through a high temperature short time ("HTST") steam heater and water cooler to ensure maximum thermal compatibility with the remainder of the process. The HTST steam heater may also sterilize the liquid feedstock. Alternatively, the liquid feedstock may be sterilized, using for example gamma or ultraviolet radiation. The solid feedstock may be received into a storage bin prior to solids pretreatment 104.

The solids from the feedstock handling phase 102 may go through a pretreatment operation 104, which may make the lignocellulosic material more amenable to the hydrolysis phase. Pretreatment may be achieved, for example, by exposure of the feedstock to an acid, base, steam, irradiation, or high temperature. The pretreatment of lignocelluloses may help separate the cellulose and hemicellulose components of lignocellulose from the lignin, as well as degrade the hemicellulose into smaller sugar oligomers.

Figure 2:
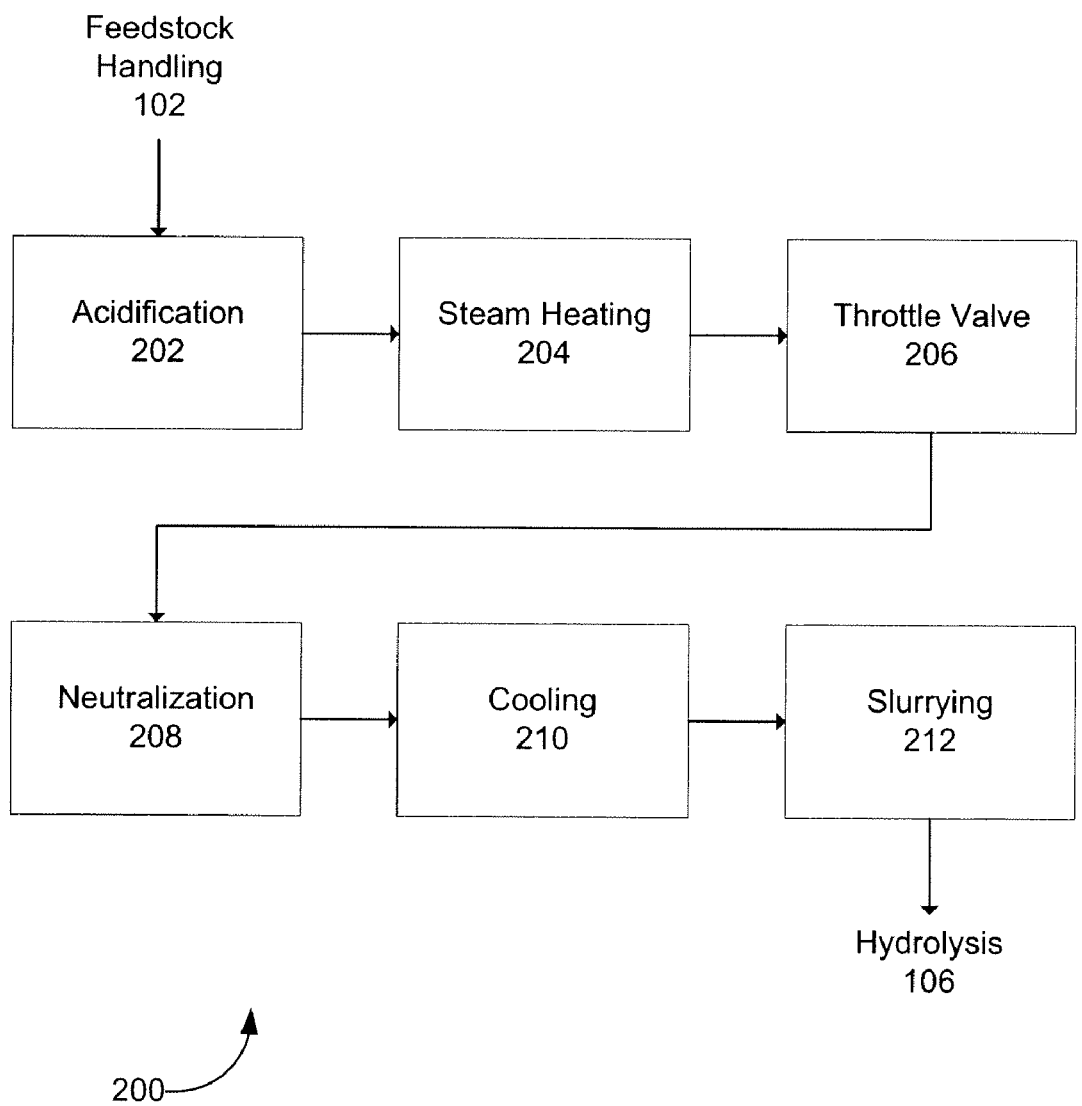
FIG. 2 is a flow diagram of one embodiment of a pretreatment stage of the process depicted in FIG. 1.

As shown in FIG. 2, in certain embodiments of pretreatment 104, the solid feedstock stream from the feedstock handling 102 is acidified 202 with sulfuric acid such that the concentration of the acid in the material coming out of a downstream throttle valve 206 is approximately 0.8% w/w. The acidified material may be heated in a steam heater 204 to a temperature of between about 325° F. to about 375° F.

Alternatively, the acidified material may be heated to a temperature of between about 345° F. to about 355° F. The addition of acid to the solid feedstock stream may be exothermic, providing an internal heat source. Alternatively, the acidified material may be heated using various methods, such as a radiant heating, as would be known by one having skill in the art with the aid of the present disclosure. The heated solid feedstock stream may be maintained at these temperatures for about 1 to 5 minutes. The heated stream is then flashed through a pressure-reducing throttle valve 206 from a pressure of approximately 80 to 170 psig to slightly above atmospheric pressure. The acidification, heating, and drop in pressure provides liquefaction and reduces the physical size of the solid feedstock material, thereby increasing its amenability to enzymatic conversion. After the pressure reduction, the stream may be neutralized 208 from a pH of about 1 to a pH of between about 5 to about 8, to provide appropriate conditions for the subsequent hydrolysis 106.

The solid feedstock stream may be cooled 210 prior to hydrolysis, using various methods. In one embodiment, the hot solid feedstock stream can be used to preheat the ethanol solution going into the distillation column (FIG. 1, 120) via a process-to-process heat exchanger as the cooling apparatus 210, or alternatively to provide heat to a step elsewhere in the original brewery process. Alternatively, the process stream may be cooled to the hydrolysis feed temperature, such as between 130° F. to 150° F., via a water-cooled exchanger as the cooling apparatus 210. After neutralization 208 and cooling 210, the solid feedstock stream may be combined with the liquid feedstock from the feedstock handling phase 102. The mixture may be slurried 212 with additional water if necessary.

In one embodiment, the pretreatment steps are performed within pipes that are in-line with the feedstock streams. For example, in one embodiment, the acidification 202 and the steam heating 204 are performed in-line, the neutralization is performed in a reaction vessel, and the cooling 210 and slurrying 212 are performed in-line.

Returning to FIG. 1, in certain embodiments, the mixed feedstock stream is then pumped to a hydrolysis reactor 106. The hydrolysis 106 step breaks the feedstock material into sugar, using hydrolytic enzymes to convert the starch and lignocellulose to simple sugars. Enzymes for use in converting feedstock into sugar may vary depending on the hydrolysis conditions and would be known by one having skill in the art with the aid of the present disclosure. Furthermore, enzymes specific for converting starch and enzymes specific for converting lignocellulose may be used simultaneously or stepwise. The enzymes generally can be used in amounts that are not particularly limited.

According to one embodiment, the hydrolysis step 106 operates in a batch manner, and may include three tanks cycling at twelve hours intervals. The tanks are filled with feedstock material and a mixture of enzymes may be used to convert the starch and lignocellulose to simple sugars. Exemplary enzymes that may be used for hydrolysis are cellulase, hemicellulase, glucoamylase, and alpha-amylase. As would be apparent to those having skill in the art with the aid of the present disclosure, other hydrolytic enzymes, including genetically modified enzymes, may also be used for the hydrolysis. A pump may provide additional mixing and temperature control via an external heat exchanger. The same pump may also be used for emptying the tank and transferring the hydrolyzed biomass to the fermentation area.

In an alternative embodiment, the hydrolysis 106 step may be accomplished in a two step process. By way of example, in the first step, the enzymes used to convert starch to simple sugars may be used. The particular reaction conditions, such as a target temperature, pH, and reaction time, may be optimized for the conversion of starch material and would be apparent to those skilled in the art with the aid of the present disclosure. Then in a second step, the enzymes used to convert lignocellulose to simple sugars may be used under conditions optimal for that specific conversion. As would be apparent to one having skill in the art with the aid of the present disclosure, the order of steps may be interchangeable.

Subsequent to the hydrolysis 106 step, the mixed feedstock stream undergoes fermentation 108. The chemicals and materials used for the fermentation phase 108 may be received, stored and prepared accordingly in a materials receiving step 110. An ethanol-producing microbe such as yeast, which converts simple sugars into ethanol, may be prepared or propagated in a yeast resuspension phase 112. As would be apparent to those having skill in the art with the aid of the present disclosure, other ethanol-producing microbes, including native and genetically modified microbes, may be used, such as *Zymomonas mobilis*, *Saccharomyces cerevisiae*, *Escherichia coli*, *Bacillus subtilis*, and *Pichia pastoris*. In a further embodiment, additional enzymes may come from materials receiving 110. Cooling water may come into this area from Utilities 114.

Similar to one embodiment of the hydrolysis 106 step, the fermentation 108 step may be performed in batches among a number of tanks so that processes before and after can operate continuously, if necessary.

In one embodiment, a given fermentation cycle may be completed in about 48 hours. A fermentation cycle refers to filling, fermenting, draining, and cleaning. Each fermentation tank may include a circulating pump and an external heat exchanger to cool the mixture, as the fermentation phase 108 may generate some heat. Also, while not specifically optimized for it, some additional hydrolysis activity may occur during fermentation.

Fermentation 108 creates ethanol and carbon dioxide from the sugars in solution. From the fermentation tank, beer (i.e., the ethanol solution), may be pumped into a beer well 116 and carbon dioxide may be sent to a scrubber 118 on the beer well 116. In one embodiment, the beer well 116 acts as a storage and surge tank allowing the batch hydrolysis and fermentation processes to be coupled to a continuous distillation process. Additional fermentation may occur here, although temperature control may not be exercised, and the beer well 116 may not be optimized for fermentation reactions.

Fermentation may also be performed on the sugars to create other alcohols, such as methanol, propanol, or other alkyl alcohols, as well as to create alkyl acids (lactic or acetic acid), or other fermentation products as would be apparent to those having skill in the art with the aid of the present disclosure, resulting from fermentation by other microbes, including native and genetically modified microbes. Fermentation may also be optional, to produce a source of sugar or sugar oligomers from the hydrolysis of the lignocellulosic material. The microbes generally can be used in amounts that are not particularly limited.

In one embodiment, the main process stream enters the beer well 116 from the tanks used in the fermentation phase 108. In the carbon dioxide recovery step 118, carbon dioxide from the fermentation 108, beer well 116, and the flash vapor from let-down pretreatment 206, enter the scrubber 118. Process water for the scrubber may be supplied into this area from Utilities 114.

Carbon dioxide and other vapor streams may be sent through a wet scrubber to remove any components entrained in the vapor. The carbon dioxide produced during fermentation 108 may bubble out through a vent in the fermentation tank or beer well 116. This gas is collected and sent through a scrubber to recover any entrained ethanol (and other volatile organic compounds ("VOCs")), and sent back to the brewery (if connected) or to another user for further refinement and use. The recovered ethanol/VOC/water solution returns to the beer well 116.

In one embodiment of the distillation 120, the beer (i.e., ethanol solution) is sent through a single distillation column to produce an approximately 35%-60% w/w ethanol/water overhead gas mixture at a positive pressure from 5 to 10 psig. Alternatively, the ethanol/water vapor mixture produced by the single distillation column may contain about 45% to about 55% ethanol. As would be apparent to one having skill in the art, the percentage of ethanol and water in the vapor mixture after a single distillation will depend upon many variables, including the type, length, efficiency, and pressure of the column. The non-ethanol and non-volatile components exit the bottom of the column as whole stillage that is then sent to stillage handling 122 for further processing.

Figure 3:
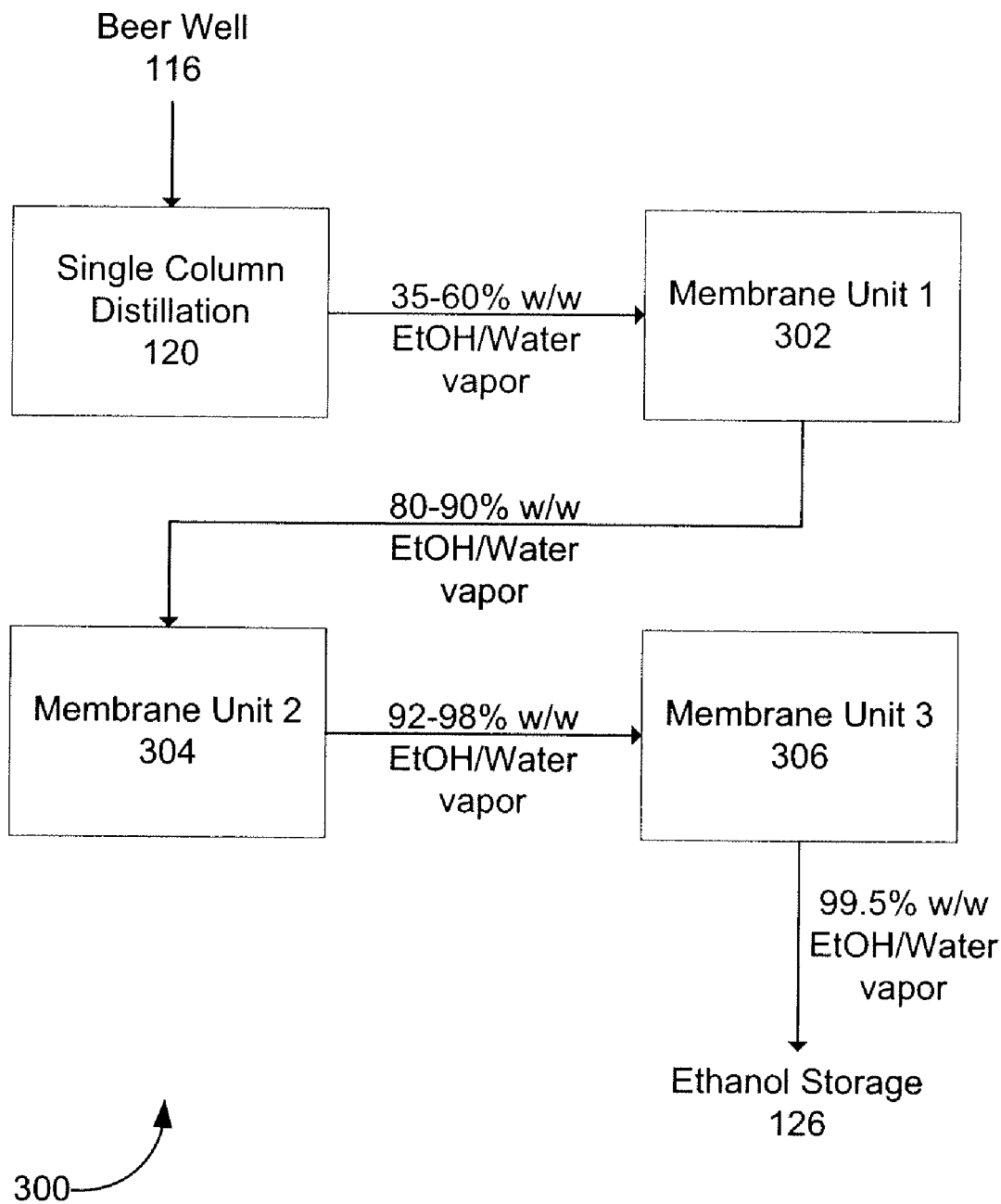
FIG. 3 is a flow diagram of one embodiment of an ethanol dehydration stage of the process depicted in FIG. 1.

In this embodiment, the gas mixture is then processed through a membrane separation system in dehydration 124 to produce anhydrous liquid ethanol. Anhydrous ethanol contains no more than about 1% water, and is also known as absolute ethanol. The membrane separation system uses a pervaporation membrane to separate water from ethanol, allowing water to flow through it more preferentially than ethanol, as shown in FIG. 3. A single distillation column 120 produces a 35-60% ethanol/water vapor mixture. In the first set of membrane units 302, which may be the largest set, the membrane retains almost all of the ethanol (less than 1% ethanol loss). The ethanol/water gas mixture now contains about 80-90% ethanol, which may be slightly pressurized prior to entering the second stage of membranes 304. The water permeate stream (vapor, ~99% water) returns to the single distillation column 120. In the second stage 304, again the membrane retains almost all of the ethanol, and this retentate stream is now between 92% and 98% ethanol. The permeate stream is mostly water, is condensed, and also returned to the single distillation column 120 at the front end of the distillation process. The retentate goes directly to the third membrane stage 306, where it is fully dewatered to at least 99.5% ethanol. This vapor stream may be used to pre-heat the beer coming into distillation 120 for heat recovery and condensation purposes, reducing the amount of energy required for the process by approximately 50%.

Returning to FIG. 1, an alternative distillation method for producing anhydrous ethanol is the use of three distillation columns 120 to separate ethanol from water and other impurities in a continuous process. Again, the non-ethanol and non-volatile components exit the bottom of the columns as whole stillage, which may be sent to stillage handling 122 for further processing.

The ethanol that exits the top of the series of three distillation columns in distillation 120 is an azeotropic mixture of ethanol and water, where, in one embodiment, the concentration of ethanol is approximately 96% w/w. Molecular sieves may be used to remove the remaining water to produce a 200-proof, or absolute, alcohol product in an ethanol dehydration step 124. Molecular sieves are a naturally occurring or synthetic zeolite with a high surface area and uniform pore size, that have the ability to adsorb gases or liquids such as water, for dehydration purposes.

In one embodiment, once the ethanol is dehydrated 124, it is denatured and stored 126. The ethanol may be sent to a 200-proof storage tank prior to denaturing. From there it may be mixed with 1.96 to 4.76% v/v denaturant and sent to a fuel ethanol storage tank 134.

The whole stillage which exits the bottom of the distillation column may enter a whole stillage processing centrifuge 122. In one embodiment, the centrifuge 122 produces two streams, namely, a centrate stream 128, which is mostly liquid (typically 1% suspended solids), and a cake stream 130, which is typically 50% solids and 50% liquid.

There are a variety of options available to the end processing steps of the centrate 128 and solid cake 130 streams after centrifugation 122. In an embodiment, the centrate 128 may be passed through a membrane to generate a clean water stream and a concentrated syrup stream. This membrane may be a cross-flow membrane that allows water and smaller-sized molecules to pass through. In order to prevent the build-up typically associated with these cross-flow type membranes, the membrane unit may be vibrated at a high rate which creates a shear cleaning force near the membrane surface, which prevents fouling that leads to decreased performance. The clean water stream coming out of the membrane may be used as slurry water for feedstock handling 102 in the early stages of the process, or at any time that additional water is needed. In one embodiment, the resulting syrup may be mixed back in with the cake. The removed solids and approximately 50% of the liquid feed may produce a stream of 2% solids, which may be combined with the cake 130 from the centrifuge 122. This combined solid product may be approximately 33% solids, and may be used as an animal or fish feed product after product loadout 132.

The whole stillage may be transformed into various other commercial products, including fuel for pellet-based heating systems. In one embodiment, the whole stillage goes through the centrifuge 122 which may extract the liquid and produce a cake. The cake may be a pelletized biomass fuel precursor configured for pelletization into a biomass pellet fuel. Biomass-derived fuels are conventionally produced from wood or grass feedstocks, and may be milled into small pellets for use in pellet stoves and boilers. Pellets may be very dense and, when produced with low moisture content, burn with high efficiency. Their standard milled size allows for compact storage, ease in transport, and an amenability for use in automatic fuel feeding systems on a boiler. The whole stillage may be recovered after fermentation or distillation of the spent brewers grain, for use as a fuel, and then further dried and pelletized for use in conventional pellet stoves and boilers. Brewery biomass may be considered a sustainable and renewable energy source, and pelletized heating fuel derived therefrom as a novel and efficient usage of a waste byproduct.

In an embodiment, a portion of the pellets may be returned to a connected brewery to supplement the brewery power source, and the offset may be used by a local power company, generating Renewable Energy Certificates (RECs) for the use of biomass. The RECs and the additional energy added to the local power grid, may be sold together or separately.

In a further embodiment, when the cake 130 is used for pellets, the centrate 128 may be further processed into a syrup-like animal feed additive. The cake 130 and syrup may also be recombined into a solid animal feed product.

In an embodiment, when the cake 130 is used for pellets, the centrate 128 may be used in an anaerobic digester. Alternatively, the entire whole stillage mixture exiting the distillation phase may bypass the centrifuge 122 and go directly to an anaerobic digester. Anaerobic digesters may produce biogas, which consists primarily of methane and carbon dioxide, which can be used to generate heat and electricity. Methane-producing microorganisms can be mesophilic, which produce methane optimally at temperatures between about 65° F. to about 100° F., or thermophilic, which produce methane at increased temperatures (between about 120° F. to about 160° F.). Anaerobic digestion also produces digestate, which is rich in nutrients and may be used as a soil fertilizer or composting material.

In an embodiment, the biogas may be scrubbed and added to existing natural gas pipelines as an additional source of natural gas. Alternatively, the biogas may be burned directly, to drive turbines that generate electricity that may be used at a connected brewery or local power plant. Renewable energy certificates (RECs) may also be involved due to this type of biomass usage, as well.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A process for converting a grain fermentation residual product into ethanol, comprising:
    A) pretreating a grain fermentation residual product with acid and heat to degrade hemicellulosic material within the grain fermentation residual product, wherein pretreating the grain fermentation residual product includes an in-line processing system, comprising:
        A1) treating the grain fermentation residual product with acid to form an acidified grain material;
        A2) steam-heating the acidified grain material in a pressurized pipe, to a temperature of between about 325° F. to about 375° F. and a pressure of between about 80 to about 170 psig;
        A3) flowing the heated and acidified grain material through a throttle valve into a reaction vessel slightly above atmospheric pressure;
        A4) neutralizing the grain material in the reaction vessel;
        A5) adding a liquid brewery feedstock or water to provide a mixed material stream; and
        A6) cooling the mixed material stream to a temperature of between about 130° F. to about 150° F. with an in-line pipe heat exchanger;
    B) hydrolyzing the pretreated grain fermentation residual product with an enzyme to convert starch and cellulosic material to simple sugars;
    C) fermenting the simple sugars into ethanol with an ethanol-producing microbe;
    D) distilling the ethanol;
    E) dehydrating the ethanol to remove water; and
    F) recovering whole stillage as an animal or fish feed product.

2. A process for converting a grain fermentation residual product into ethanol, comprising:
    A) pretreating a grain fermentation residual product with acid and heat to degrade hemicellulosic material within the grain fermentation residual product;
    B) hydrolyzing the pretreated grain fermentation residual product with an enzyme to convert starch and cellulosic material to simple sugars;
    C) fermenting the simple sugars into ethanol with an ethanol-producing microbe;
    D) distilling the ethanol, wherein distilling the ethanol comprises:

D1) distilling the ethanol with a single distillation column to provide an ethanol/water mixture of between about 35% to about 60% w/w ethanol;
E) dehydrating the ethanol to remove water, wherein dehydrating the ethanol comprises:
E1) flowing the ethanol/water mixture from the single distillation column through a series of three pervaporative membranes to remove water from the ethanol; and
F) recovering whole stillage as an animal or fish feed product.

3. A process for converting a grain fermentation residual product into ethanol, comprising:
A) pretreating a grain fermentation residual product with acid and heat to degrade hemicellulosic material within the grain fermentation residual product;
B) hydrolyzing the pretreated grain fermentation residual product with an enzyme to convert starch and cellulosic material to simple sugars;
C) fermenting the simple sugars into ethanol with an ethanol-producing microbe;
D) distilling the ethanol, wherein distilling the ethanol comprises:
D1) distilling the ethanol with a single distillation column to provide an ethanol/water mixture of between about 35% to about 60% w/w ethanol;
E) dehydrating the ethanol to remove water, wherein dehydrating the ethanol comprises:
E1) treating the ethanol/water mixture with molecular sieves to remove water from the ethanol; and
F) recovering whole stillage as an animal or fish feed product.

4. The process of claim 1, further comprising:
denaturing the dehydrated ethanol for the production of fuel ethanol.

5. The process of claim 1, wherein the grain fermentation residual product comprises at least one of the group consisting of spent brewers grain and residual distillers grain products.

6. The process of claim 2, further comprising:
denaturing the dehydrated ethanol for the production of fuel ethanol.

7. The process of claim 2, wherein the grain fermentation residual product comprises at least one of the group consisting of spent brewers grain and residual distillers grain products.

8. The process of claim 3, further comprising:
denaturing the dehydrated ethanol for the production of fuel ethanol.

9. The process of claim 3, wherein the grain fermentation residual product comprises at least one of the group consisting of spent brewers grain and residual distillers grain products.

* * * * *